(12) United States Patent
Lascola

(10) Patent No.: US 10,293,062 B2
(45) Date of Patent: May 21, 2019

(54) METAL COMPLEXES WITH BISPHOSPHONATE USEFUL AS IMAGING AGENTS

(71) Applicant: Duke University, Durham, NC (US)

(72) Inventor: Christopher David Lascola, Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 15/463,688

(22) Filed: Mar. 20, 2017

(65) Prior Publication Data

US 2017/0189562 A1 Jul. 6, 2017

Related U.S. Application Data

(63) Continuation of application No. PCT/US2016/028946, filed on Apr. 22, 2016.

(60) Provisional application No. 62/152,417, filed on Apr. 24, 2015.

(51) Int. Cl.
| | | |
|---|---|---|
| *A61B 5/055* | (2006.01) | |
| *A61K 49/10* | (2006.01) | |
| *A61K 49/08* | (2006.01) | |
| *A61K 47/54* | (2017.01) | |

(52) U.S. Cl.
CPC .......... *A61K 49/101* (2013.01); *A61K 47/548* (2017.08); *A61K 49/085* (2013.01); *A61K 49/103* (2013.01); *A61K 49/106* (2013.01)

(58) Field of Classification Search
None
See application file for complete search history.

(56) References Cited

U.S. PATENT DOCUMENTS

| 8,247,572 B2 | 8/2012 | Kraus et al. | |
|---|---|---|---|
| 2010/0247607 A1* | 9/2010 | Ashton | A61K 9/0024 424/426 |
| 2014/0234210 A1* | 8/2014 | Lin | A61K 9/14 424/1.21 |
| 2014/0350193 A1 | 11/2014 | Axelsson et al. | |
| 2015/0191471 A1 | 7/2015 | Haystead et al. | |

OTHER PUBLICATIONS

Kushikbaeva et al. (Inorg. Chem. 1988, 2455-2460).*
Noebauer-Huhmann et al. (Invest. Radiol. 2010, 45, 554-558).*
Caravan P et al. Influence of molecular parameters and increasing magnetic field strength on relaxivity of gadolinium- and manganese-based T1 contrast agents. Contrast Media Molecular Imaging; Mar.-Apr. 2009; 4(2) 89-100.
Sergienko VS et al. Crystal structure of triethanolammonium bis(1-hydroxyethane-1,1-diphosphonato)diaquazincate pentahydrate, [OHCH2CH2)3NH][Zn(H2O)2(H2.5L)2] 5H2O. Crystallography Reports. 2000; 45(2): 262-265.
Sergienko VS. Structural chemistry of 1-hydroxyethylidenediphosphonic acid complexes. Russian Journal of Coordination Chemistry. 2001; 27(10): 681-710.
International Search Report and Written Opinion, PCT/US2016/028946, dated Jul. 1, 2017.
International Search Report and Written Opinion, PCT/US2016/058845, dated Jan. 13, 2017.
Lascola C et al. Drivable high spin FE(III) and Mn(II) phosphonate scaffolds for MRI. International Society for Magnetic Resonance in Medicine, ISMRM, 2030 Addison Street, 7th Floor, Berkeley, CA 94701 USA. No. 2846, Apr. 25, 2014. Abstract.
Lascola C et al. Drivable high spin FE(III) and Mn(II) phosphonate scaffolds for MRI. Joint Annual Meeting of International Society for Magnetic Resonance in Medicine, ESMRMB, Milan, Italy. May 12-15, 2014. Poster.
Demoro B et al. Bisphosphonate metal complexes as selective inhibitors of Trypanosoma cruzi farnesyl diphosphate synthase. Dalton Trans. 2012; 41: 6468-6476.
Crisponi G et al. Potentiometric and spectrophotometric equilibrium study on Fe(III) and new catechol-bisphosphonate conjugates. Journal of Inorganic Biochemistry. 2008; 102: 209-215.
El-Mabhouh AA et al. A 99mTc-labeled gemcitabine bisphosphonate drug conjugate as a probe to assess the potential for targeted chemotherapy of metastatic bone cancer. Nuclear Medicine and Biology. 2006; 33: 715-722.
Hosain F et al. Targeted delivery of antineoplastic agent to bone: biodistribution studies of technetium-99m-labeled gem-bisphosphonate conjugate of methotrexate. J Nucl Med. 1996; 37: 105-107.
European Patent Office Examination Report, EP 16721317.2, dated Sep. 22, 2017.
Japanese Office Action corresponding to Japanese Patent Application No. 2017-524038, dated Feb. 27, 2018. 7 pages.

* cited by examiner

*Primary Examiner* — Johann R Richter
*Assistant Examiner* — Melissa J Perreira
(74) *Attorney, Agent, or Firm* — Myers Bigel, P.A.

(57) ABSTRACT

Provided herein are magnetic resonance imaging (MRI) contrast agents comprising a compound having a structure represented by: Y—X—Z, wherein, X is: Fe(III) or Mn(II), and Y and Z are each independently selected from pyrophosphate and bisphosphonate (e.g., 1-hydroxybisphosphonate), or a pharmaceutically acceptable hydrate and/or salt thereof. Methods of use of the MRI contrast agent are also provided.

20 Claims, 7 Drawing Sheets

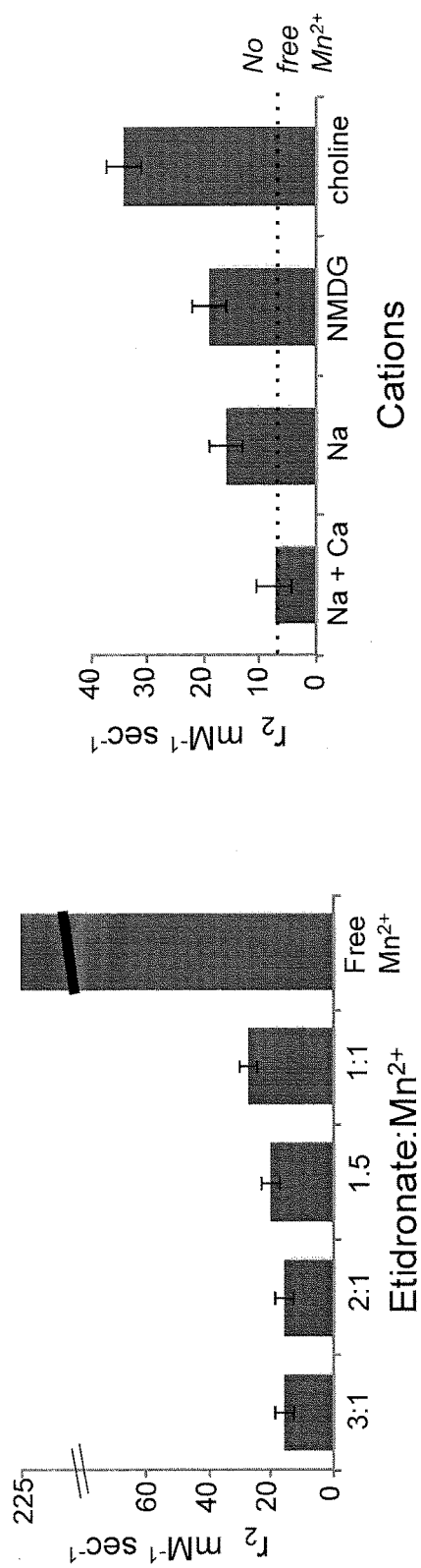
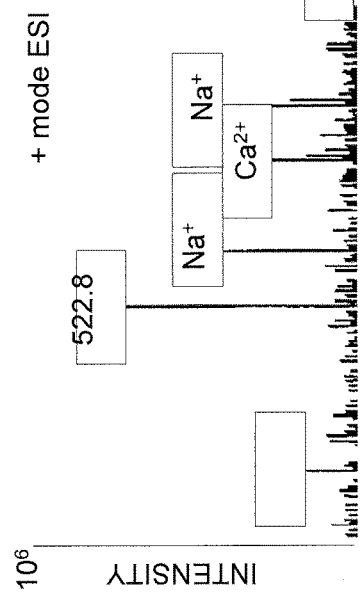
FIG. 3A
FIG. 3B
FIG. 3C

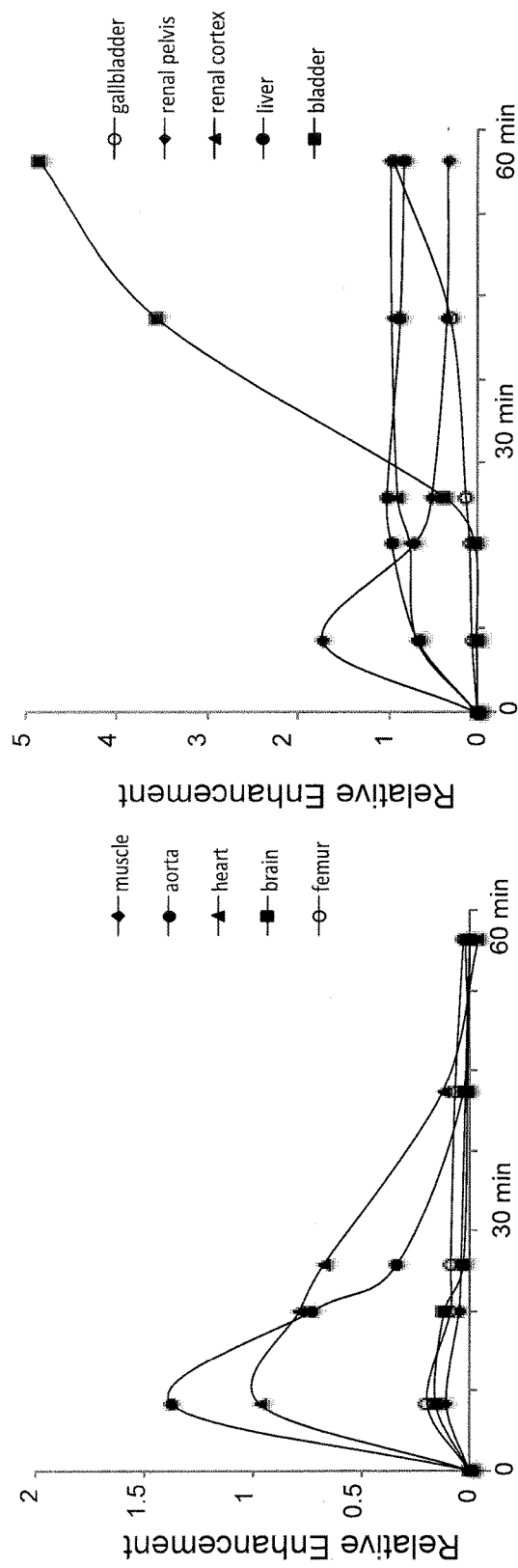
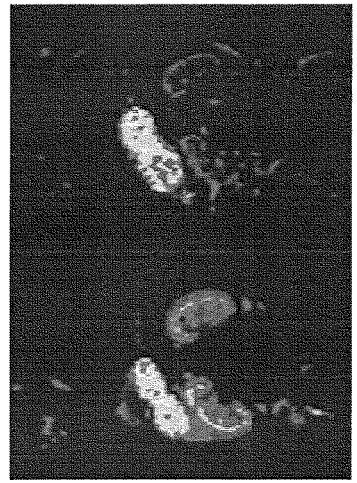
FIG. 6B
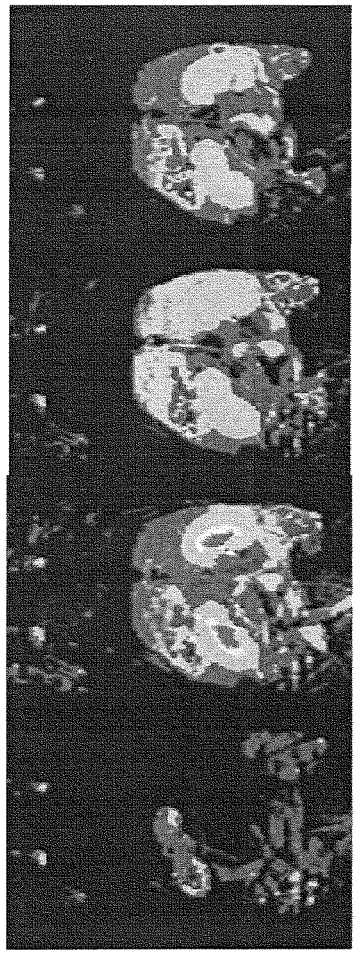
FIG. 6C
FIG. 6A

METAL COMPLEXES WITH BISPHOSPHONATE USEFUL AS IMAGING AGENTS

RELATED APPLICATIONS

This application is a continuation under 35 U.S.C. 111(a) of PCT/US2016/028946, filed Apr. 22, 2016, which in turn claims the benefit of U.S. Provisional Patent Application Ser. No. 62/152,417, filed Apr. 24, 2015, the disclosure of each which is incorporated by reference herein in its entirety.

GOVERNMENT FUNDING

This invention was made in part with government support under grant number W81XWH-12-1-0447 awarded by the Department of Defense. The United States government has certain rights in the invention.

BACKGROUND

The most advanced diagnostic imaging modalities, computed tomography (CT) and magnetic resonance imaging (MRI), produce exquisite renderings of human anatomy and pathology at high spatial resolution. These "cross-sectional" imaging modalities represent the gold-standard for diagnostic assessment, characterization and monitoring of treatment response for complex disease processes, and are utilized for every region and organ system in the human body.

To increase diagnostic sensitivity and specificity for CT and MRI studies in cancer, infection, neurological and heart diseases, contrast material is often administered intravenously before and/or during imaging to improve detection and characterization of these disease processes. For CT, the most common contrast media are based on iodine, which has a "k-edge" that is ideal for clinical x-ray absorption.

For MRI, the most common contrast material is based on molecular complexes containing the paramagnetic metal gadolinium (Gd). In the U.S., all nine FDA-approved MRI contrast agents are Gd-based. Gd possesses strong "paramagnetism" that results in a locally increased MRI signal on $T_1$-weighted images. However, Gd-based contrast agents can cause a rare but severely debilitating condition called nephrogenic systemic fibrosis (NSF), a syndrome involving widespread fibrosis of the skin, joints, eyes, and internal organs. The WHO and FDA have issued restrictions on the use of these agents in patients with renal insufficiency/failure, with the FDA mandating a "black box" warning on all commercial media containing gadolinium. As a consequence, millions of patients in the US, and many more worldwide, are no longer able to receive contrast material for MRI, severely limiting detection and characterization for several diseases.

Other paramagnetic complexes, used more rarely either as investigational or as "off-label", are usually based on large iron oxide-based nanoparticles developed and marketed as intravenous iron replacement therapy (e.g., FERAHEME® (ferumoxytol) injection). The use of these complexes for MRI is limited, however, by their poor $T_1$ relaxation properties, strong $T_2^*$ relaxation properties, resulting in decreased MRI signal ("negative contrast"), and large molecular size, which confines these agents to the blood pool until they are finally cleared by the reticuloendothelial system (i.e., macrophages, liver, spleen).

Thus, alternative contrasting agents useful for MRI and similar scanning technologies are needed.

SUMMARY

Provided herein according to some embodiments is a magnetic resonance imaging (MRI) contrast agent comprising a compound having a structure represented by:

wherein,
X is: Fe(III) or Mn(II); and
Y and Z are each independently selected from pyrophosphate and bisphosphonate (e.g., 1-hydroxybisphosphonate),
or a pharmaceutically acceptable hydrate and/or salt thereof.

In some embodiments, X is Mn(II) and Y and Z are each independently a bisphosphonate of the formula:

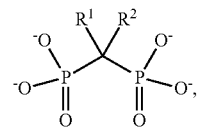

wherein: $R_1$ is —OH, and $R_2$ is selected from the group consisting of: H, alkyl, aminoalkyl, alkylaminoalkyl, arylalkyl, and heteroarylakyl, or a pharmaceutically acceptable hydrate and/or salt thereof.

In some embodiments, the MRI contrast agent has a molecular weight less than 2,000 daltons or less than 800 daltons.

In some embodiments, the compound is octahedral. In some embodiments, the compound is a monohydrate or a dihydrate. In some embodiments, the compound is a salt comprising from 1 to 3 cations.

In some embodiments, the X is Mn(II) and Y and Z are each bisphosphonate (e.g., 1-hydroxybisphosphonate).

In some embodiments, the X is Fe(III) and X and Z are each pyrophosphate.

In some embodiments, the compound is coupled to one or more therapeutic agents (e.g., a chemotherapeutic agent). In some embodiments, the one or more therapeutic agents are covalently coupled to Y and/or Z.

Also provided is a composition comprising an MRI contrast agent as described herein in a pharmaceutically acceptable carrier (e.g., sterile water or a sterile buffer such as phosphate buffered saline). In some embodiments, the composition is formulated for intravenous or intraarterial administration (e.g., isotonic with blood). In some embodiments, the composition has a pH of from 7.0 to 7.4.

Also provided is a method of performing a MRI scan on a subject comprising administering a contrast agent to said subject prior to and/or during said MRI scan.

Further provided is a method of administering a therapeutic agent to a subject in need thereof, comprising administering a contrast agent coupled to a therapeutic agent to said subject in a treatment effective amount. In some embodiments, the method further comprises detecting the contrast agent with MRI in said subject.

Also provided is the use of a MRI contrast agent as taught herein for performing a MRI scan or administering a therapeutic agent to a subject in need thereof.

BRIEF DESCRIPTION OF THE DRAWINGS

FIG. 3A. A 2:1 complex of 1-OH bisphosphonate and $Mn^{2+}$ is thermodynamically favored. By varying stoichiometry during synthesis, no additional complexation of $Mn^{2+}$ is observed when the ratio of bisphosphonate to $Mn^{2+}$ is raised above 2:1. Free $Mn^{2+}$ is determined by measuring solvent $T_2$ as a function of time, since $r_2$ of $Mn^{2+}$ is 30-fold that of fully chelated, monohydrated $Mn^{2+}$ (Caravan et al., Mol. Imaging 2009, 4:89).

FIG. 3B. Alkali metal cations increase the stability of the 2:1 bisphosphonate:$Mn^{2+}$ complex. Heteronuclear complexes containing at least one $Na^+$ cation and at least one $Ca^{2+}$ cation form the most stable 2:1 complexes, resulting in complete chelation of mono-hydrated $Mn^{2+}$ without excess ligand. Horizontal dotted line indicates the point at which $r_2$ becomes 30-fold less than the value of $MnCl_2$ in solution.

FIG. 3C. ESI MS of a heteronuclear 2:1 etidronate: Mn complex two months after synthesis, confirming its stability and stoichiometry. $C_4H_9O_{14}P_4$:$Mn^{2+}$:$Ca^{2+}$:$Na^+$ (m/z=522.8).

FIGS. 6A-6C. PK and biodistribution of 2:1 etidronate:$Mn^{2+}$ complex synthesized with $Na^+$ and $Ca^{2+}$ ($C_4H_9O_{14}P_4$:$Mn^{2+}$:$_xCa^{2+}$:$_xNa^+$).

FIG. 6A. Dynamic contrast-enhanced (DCE) analysis of contrast agent over 60 mins following intravenous administration. Peak enhancement in organs and musculoskeletal system tracks in time with changes in aorta, indicating the contrast agent remains intact and extracellular.

FIG. 6B. DCE analysis of excretory systems shows intact elimination through kidneys and liver/gallbladder.

FIG. 6C. Normalized color lute T1 weighted images showed relative changes in organ systems over the first 60 mins, then at 24 and 48 hours. At 24 hours, no residual contrast changes are seen throughout the subject except in kidneys. The latter changes are nearly resolved by 48 hours. Higher signal intensity changes in the stomach at 24 and 48 hours (left upper quadrant) are secondary to incidental paramagnetism in the feed.

FIG. 7A. Molecular diagram of $Fe(P_2O_7)_2$ illustrating two inner sphere coordinating waters.

FIG. 7B. ESI MS of the complex. That this complex remains intact under ESI conditions is further evidence of its stability.

FIG. 7C. Paramagnetic complex iron complex formed from thiamine pyrophosphate.

FIG. 7D. Positive mode ESI MS of paramagnetic iron thiamine pyrophosphate complex. * $C_{24}H_{34}N_8O_{14}P_4S_2Fe$ (m/z=902); ** $C_{24}H_{34}N_8O_{14}P_4S_2Fe+C_7H_{17}NO_5$ [meglumine] (m/z=1097); $C_{24}H_{34}N_8O_{14}P_4S_2Fe-N_3C_6H_7$ [aminodimethylpyridine fragment) (m/z=781); $C_{24}H_{34}N_8O_{14}P_4S_2Fe-(2)N_3C_6H_7$ (m/z=660).

DETAILED DESCRIPTION

Figure 1:
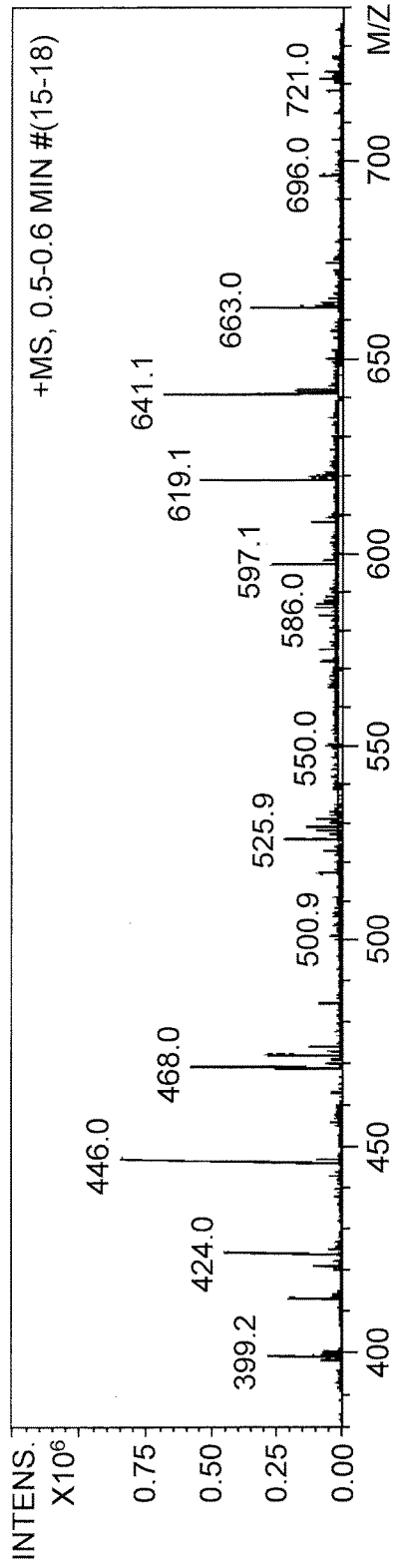
FIG. 1. Positive mode ESI MS of paramagnetic Na:Mn (Etidronate)$_2$ complex with additional Na or meglumine as salt adducts. Each represents the bass peak of the designated complex after loss of the $PO_3$ fragment during ionization. 1Na: $C_4H_{11}O_{11}P_3$:Mn:$H_2O$ (m/z=424). 2Na:$C_4H_{10}O_{11}P_3$:Mn:$H_2O$ (m/z=446) 3Na:$C_4H_9O_{11}P_3$:Mn:$H_2O$ (m/z=468) 1Na:$C_4H_{11}O_{11}P_3$:Mn:$H_2O$:$C_7H_{17}NO_5$ (m/z=619.1) 2Na: $C_4H_{10}O_{11}P_3$:Mn:$H_2O$:$C_7H_{17}NO_5$ (m/z=641.1) 3Na: $C_4H_9O_{11}P_3$:Mn:$H_2O$:$C_7H_{17}NO_5$ (m/z=663.0)
Figure 2:
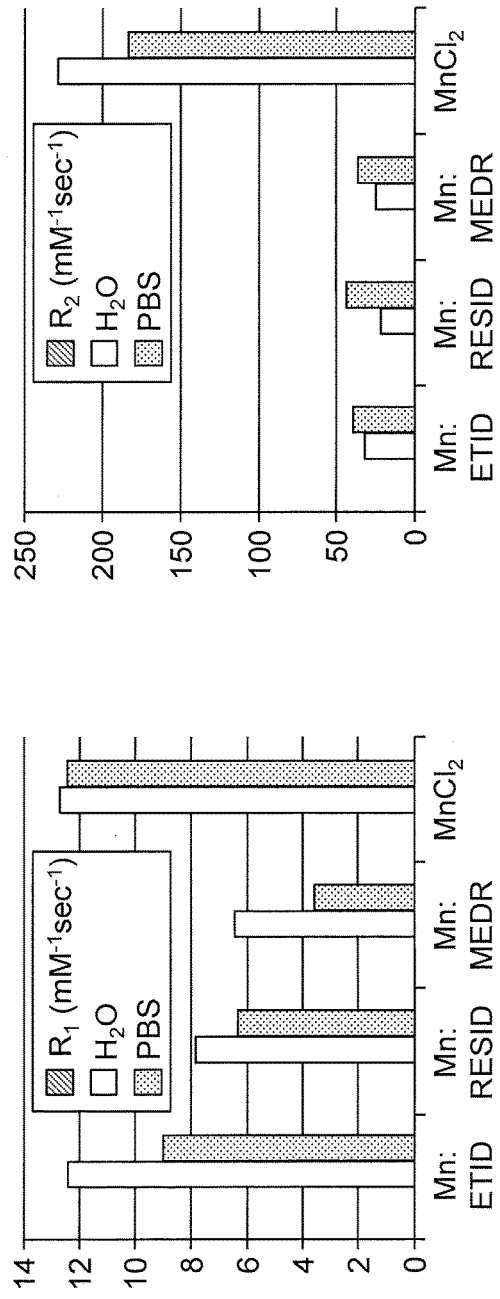
FIG. 2. $T_1$ and $T_2$ relaxivities ($r_1$, left and $r_2$, right) of Mn bisphosphonate complexes with commercially available bisphosphonates, as compared to free Mn(II).

The disclosures of all patent references cited herein are hereby incorporated by reference to the extent they are consistent with the disclosure set forth herein. As used herein in the description of the invention and the appended claims, the singular forms "a," "an" and "the" are intended to include the plural forms as well, unless the context clearly indicates otherwise.

Provided herein are compounds useful as contrast agents. "Compound" as used herein refers to a molecule having atoms held together via covalent, coordinate and/or ionic bonds.

"Contrast agent" as used herein is a substance used to enhance the contrast of structures or fluids within the body in medical imaging. Examples of known contrast agents include, but are not limited to, radiocontrast agents and MRI contrast agents.

A "radiocontrast agent" is a substance that can enhance the contrast of structures or fluids within the body during an x-ray-based scan. Examples include, but are not limited to, iodine and barium.

An "MRI contrast agent" is a substance (e.g., compound and/or complex) that can enhance the contrast of structures or fluids within the body during an MRI scan. Examples include, but are not limited to, paramagnetic contrast agents such as gadolinium(III) containing agents or manganese chelates, and superparamagnetic agents such as iron platinum particles. See also U.S. Patent Application Publication Nos. 2014/0350193 to Axelsson et al.; 2014/0234210 to Lin et al.

In some embodiments, the use of a contrast agent of the present invention may enhance contrast (also known as "attenuation" in CT, "signal" in MRI) of tissues such as arteries and veins of a subject, greatly improving delineation of vessel anatomy and pathology. Examples of vascular diseases that can be detected with contrast include atherosclerotic plaque, thrombosis, vascular malformations, aneurysms, and arterial dissections.

In some embodiments, the use of a contrast agent of the present invention may enhance "attenuation" or "signal" in diseased tissues of a subject where contrast material transiently accumulates in the extracellular compartment (interstitium) of diseased regions after the "first pass" through the blood vessels. Accordingly, tissue enhancement is often observed in tumors, infection, inflammation, demyelination, and acutely infarcted tissue.

In some embodiments, contrast agents as taught herein have a molecular weight of less than 2,000 daltons, 1,500 daltons, 1,000 daltons, 800 daltons, or 500 daltons. Such low molecular weight agents may enhance the imaging of tissues by, e.g., allowing diffusion from blood through diseased "leaky" blood vessels.

In some embodiments, contrast agents comprise high spin iron (Fe(III)) or high spin manganese (Mn(II)), each having 5 unpaired electrons, complexed with pyrophosphate and/or bisphosphonate.

Specific examples of bisphosphonates that may be used to carry out the present invention include, but are not limited to, alendronate, risedronate, clodronate, tiludronate, ibandronate, incadronate, zolendronate, pamidronate, medronate, minodronate, neridronate, olpadronate, tiludronate, etidronate (1-hydroxyethylenebisphosphonate) and salts and/or esters thereof.

In some embodiments, the bisphosphonate is a 1-hydroxybisphosphonate.

In some embodiments, the bisphosphate has a formula:

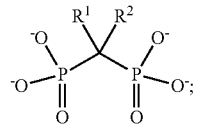

wherein: $R_1$ is —OH; and $R_2$ is selected from the group consisting of: H, alkyl, aminoalkyl, alkylaminoalkyl, arylalkyl, and heteroarylalkyl.

"Alkyl," as used herein, refers to a saturated straight or branched chain, or cyclic hydrocarbon containing from 1 to 10 carbon atoms (i.e., $C_{1-10}$). Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, cyclopropyl, cyclobutyl, cyclopentyl, cyclohexyl, and the like. "Lower alkyl" as used herein, is a subset of alkyl and refers to a straight or branched chain hydrocarbon group containing from 1 to 4 carbon atoms. Representative examples of lower alkyl include, but are not limited to, methyl, ethyl, n-propyl, iso-propyl, n-butyl, iso-butyl, tert-butyl, cyclopropyl, cyclobutyl, and the like. The alkyl groups may be optionally substituted with one or more suitable substituents, such as halo, hydroxy, carboxy, amine, etc.

"Aryl," as used herein, refers to a monocyclic carbocyclic ring system or a bicyclic carbocyclic fused or directly adjoining ring system having one or more aromatic rings. Examples include, but are not limited to, phenyl, indanyl, indenyl, tetrahydronaphthyl, and the like. As noted, in some embodiments, the aryl has two aromatic rings, which rings are fused or directly adjoining. Examples include, but are not limited to, biphenyl, napthyl, azulenyl, etc. The aryl may be optionally substituted with one or more suitable substituents, such as alkyl, halo, hydroxy, carboxy, amine, etc.

"Heteroaryl," as used herein, refers to a monovalent aromatic group having a single ring or two fused or directly adjoining rings and containing in at least one of the rings at least one heteroatom (typically 1 to 3) independently selected from nitrogen, oxygen and sulfur. Examples include, but are not limited to, pyrrole, imidazole, thiazole, oxazole, furan, thiophene, triazole, pyrazole, isoxazole, isothiazole, pyridine, pyrazine, pyridazine, pyrimidine, triazine, and the like. As noted, in some embodiments, the heteroaryl has two aromatic rings, which rings are fused or directly adjoining. Examples include, but are not limited to, benzothiophene, benzofuran, indole, benzoimidazole, benzthiazole, quinoline, isoquinoline, quinazoline, quinoxaline, phenyl-pyrrole, phenyl-thiophene, etc. The heteroaryl may be optionally substituted with one or more suitable substituents, such as alkyl, halo, hydroxy, carboxy, amine, etc.

Unless indicated otherwise, nomenclature used to describe chemical groups or moieties as used herein follow the convention where, reading the name from left to right, the point of attachment to the rest of the molecule is at the right-hand side of the name. For example, the group "aryl$C_{1-6}$ alkyl," is attached to the rest of the molecule at the $C_{1-6}$alkyl end.

Unless indicated otherwise, where a chemical group is described by its chemical formula, including a terminal bond moiety indicated by "—," it will be understood that the attachment is read from left to right.

High spin Mn(II) is an excellent candidate paramagnetic metal possessing 5 unpaired electrons, favorable electronic relaxation and water residence times ($T_m \ll T_1$) for MRI enhancement. As a free metal, Mn is also less toxic than Gd, with a natural pool and several homeostatic mechanisms for processing.

In the past, development of paramagnetic Mn complexes for MRI has been challenged by the inherent coordination lability of Mn(II) (e.g., Irving Williams series), resulting in the propensity of Mn(II) to be trans-metallated by other endogenous metals such as zinc in vivo. However, the Mn(II) bisphosphonate complex disclosed herein has a remarkable in vivo stability, remaining intact when used either alone as a tissue contrast material or coupled to other small molecule drugs. When used alone, it is eventually eliminated either through the kidneys and liver/gallbladder/bowel on a time course similar to commercial Gd-based contrast materials.

In some embodiments, the Mn bisphosphate compound has a stoichiometry of: 1 Mn:2 bisphosphonate (e.g., etidronate); has at least one coordinated $H_2O$ (e.g., monohydrate or dihydrate); has at least one alkali metal (e.g., Na+, K+) or alkaline earth metal (e.g., Ca++ or Mg++); and/or has at least one additional cation (e.g., Na+, meglumine, etc.).

In some embodiments, the contrast agent has an $r_2$ relaxivity of 5, 8 or 10 to 15, 18, 20, 25, 30, 35 or 40 $mM^{-1}sec^{-1}$ measured at 7 Tesla (e.g., at 22 degrees Celsius, 2 mM Tris buffered dd$H_2O$, and/or pH 7.0). Without wishing to be bound by theory, free Mn in solution (e.g., $MnCl_2$ salt) has low $T_2$ relaxation/high $r_2$ relaxivity ($mM^{-1}sec^{-1}$) because of both increased T2* susceptibility as well as spin-spin (T2') effects. T2 (and, thus, r2) are a function of both T2* and T2'. Hydrated, free ions cluster together with several coordinating inner sphere waters, increasing local magnetic field inhomogeneity and spin-spin interactions between bound and solvent water molecules. When individual Mn ions are coordinated with a ligand, clustering, and, therefore, T2* effects (and $r_2$ relaxivity) are reduced. Strong Mn complexes with only one coordinating inner sphere water also possess decreased spin-spin interactions, and, therefore, T2' effects by virtue of less exchange between bound and solvent water molecules. When individual Mn ions become fully complexed with a ligand chelate in solution, measured $r_2$ of the chelate metal has been previously determined to be 30 fold less than the free metal in solution. See Caravan et al., Mol. Imaging 2009, 4:89. Thus $r_2$ can be a marker of the degree of complexation. See also FIGS. 3A-3C.

The complexation of the metal may lead to reduced toxicity and/or increased stability of the contrast agent. Free metal such as Mn administered intravenously can have immediate deleterious toxicity effects. For free Mn, in particular, cardio toxicity may be a concern because of negative chronotropic/ionotropic effects. PK/biodistribution differences are seen, e.g., with 1:1 Mn:bisphosphonate complex versus the 1:2 complex, as well as with synthesis with cations such as meglumine and choline instead Na+ and Ca++ (data not shown). Toxicity may also been detected during injections, with rapid cardio and respiratory suppression at equivalent doses that is not seen with Na+ and Ca++ 1:2 Mn:bisphosphonate complexes (data not shown).

In some embodiments, a complex as taught herein may comprise one or more therapeutic agents. In these embodiments, real-time monitoring of the delivery of the therapeutic agent(s) may be performed by detection of the complex. The therapeutic agent may be complexed with the contrast agent or covalently attached to a ligand therein, directly or through a linker.

In some embodiments, the bisphosphonate may be coupled directly to a therapeutic agent prior to metal complexation. In some embodiments, the therapeutic agent is coupled directly to the bridging carbon between the phosphonates of the bisphosphonate. In some embodiments, the bisphosphonate is coupled to the therapeutic agent via the phosphate ester. In some embodiments, the bisphosphonate is coupled to a therapeutic agent via a linker (e.g., an alkylene, alkylenecarbonyl, carbonylalkylene, a carbonyl group, maleimide, PEG, etc.), prior to metal complexation. See also U.S. Pat. No. 8,247,572 to Kraus et al.

The present invention is primarily concerned with the scanning and/or treatment of human subjects, but the invention may also be carried out on animal subjects, particularly mammalian subjects such as mice, rats, dogs, cats, livestock and horses for veterinary purposes, and for drug screening and drug development purposes.

The term "treat" as used herein refers to any type of treatment that imparts a benefit to a patient afflicted with a disease, including improvement in the condition of the patient (e.g., in one or more symptoms), delay in the progression of the disease, etc.

The term "pharmaceutically acceptable" as used herein means that the compound or composition is suitable for administration to a subject to achieve the treatments described herein, without unduly deleterious side effects in light of the severity of the disease and necessity of the treatment.

The present invention is explained in greater detail in the following non-limiting examples.

EXAMPLES

Example 1: Low Molecular Weight Manganese Bisphosphonate Complex for Molecular Imaging and Multiplexed Therapy Example Synthesis of High-Spin Mn(II) Complex To a desired final volume of double distilled water and under constant stirring, add 2 equivalents of etidronic acid and 4 equivalents of sodium bicarbonate. pH of the solution will be ~3.8-4.0 after 10 minutes. The pH may then be adjusted further by dilute NaOH to ~5.5-7.0. Following this, 1 equivalent of $MnCl_2$ is added. After $MnCl_2$ addition, the solution will, as expected, become more acidic (pH~3-4), but pH should be raised with moderately dilute base such as NaOH to 7.0-7.5. The most consistent and effective results have been achieved when the pH is between 5-7 before addition of Mn(II), and an alkali metal cation (e.g., Na) is present in advance to coordinate at least with the two phosphate oxygens on etidronate which have pKa's of 0.70 and 1.46.

A mildly basic amine buffer such as Tris may be employed initially or after addition of primary reagents with good result to ensure a pH of neutrality or greater, although at least two Na+ equivalents per molecule of etidronic acid before addition of Mn seems particularly beneficial. Heat for this reaction is not necessary.

As with the iron pyrophosphate complex discussed in Example 3 below, the product may be precipitated and isolated with excess polar organic solvent (e.g., acetone, MeOH, ETOH), however this particular complex is more soluble (less hydrophilic) in these solvents and so precipitation and isolation requires more time and challenge. Alternative isolation of final solid product is also achievable by direct freeze-drying.

Figures 4A, 4B:
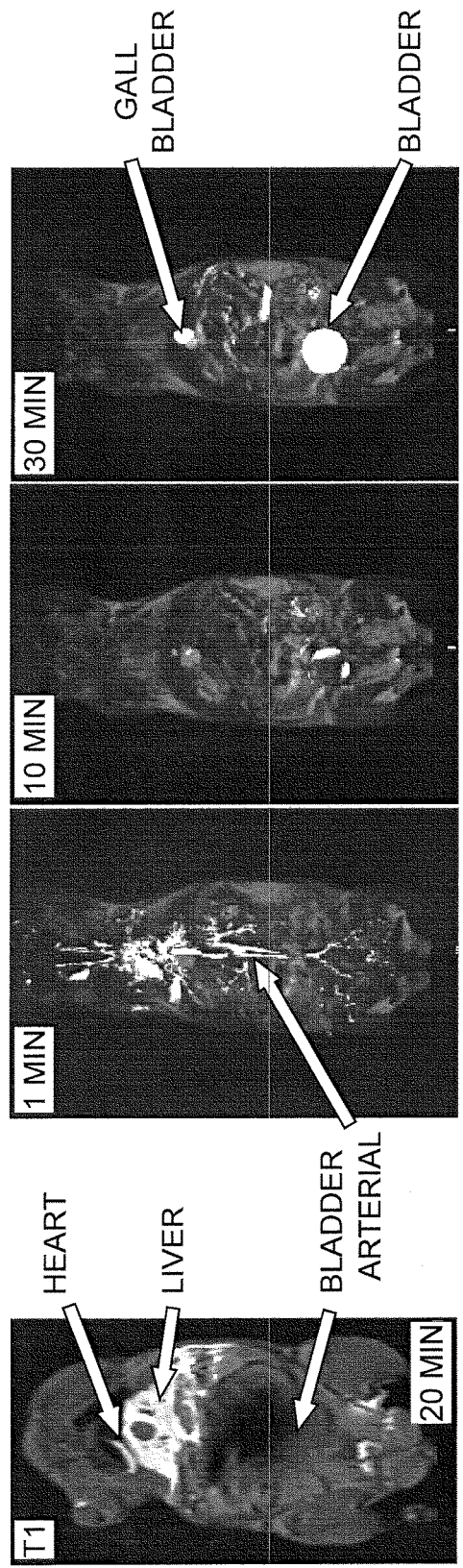
FIG. 4A. In vivo MRI in control mouse after i.v. administration of MnNTA.
FIG. 4B. MRI after i.v. administration of Mn:ETID (50 μL of 40 mM solution).

In vivo behavior was tested of two relatively strong (log $K_1$>7) ligands for Mn(II) chelation, nitrilotriacetic acid (NTA), closely related to EDTA, and 3,4-dihydrobenzoic acid (3,4-DBA). Both readily form Mn(II) coordination complexes and show relaxation profiles similar to commercial Gd chelates. In vivo MR imaging of these agents after i.v. administration, however, revealed identical biodistributions for both NTA and 3,4-DBA, consistent with release of free Mn and hepatocellular uptake, i.e., strong parenchymal enhancement, absence of gallbladder enhancement, and no evidence for renal elimination (FIG. 4A).

This in vivo behavior was also what is observed for the FDA-approved agent Teslascan. In the past, development of paramagnetic Mn complexes for MRI has been challenged by the inherent coordination lability of Mn(II) (e.g., Irving Williams series), resulting in the propensity of Mn(II) to be trans-metallated by other endogenous metals such as zinc in vivo. The only FDA-approved approved Mn(II) PM complex for MRI was Teslascan, which has now been discontinued. Teslascan immediately distributed to the liver, releasing free Mn that was then taken up by hepatocytes. Contrast enhancement was therefore based on free Mn and confined to the liver. In addition, cardiac enhancement was also seen for both NTA and 3,4-DBA, indicating free Mn released into the blood pool before entering the liver.

In comparison to NTA and 3,4-DBA, i.v. administration of 30 mg/kg Mn(II)etidronate initially reveals a striking arterial blood pool phase, followed by rapid enhancement of the renal collecting system and urinary bladder as well as gallbladder (FIG. 4B) Enhancement of the liver parenchyma is observed, although substantially less intense than NTA and 3,4-DBA, peaking at 10-15 minutes after administration and returning to normal $T_1$ values by 4 hours. Enhancement of the bowel is also noted but more variable, believed to represent elimination of the coordination complex from the gallbladder into the small intestine. In addition, subtle but transient $T_1$ changes are observed in the skeletal muscles and long bones that return to normal after 30 min, paralleling the mild residual $T_1$ changes in major vessels, consistent with a blood pool rather than local parenchymal uptake effect. No $T_1$ changes are observed in brain or spine (n=20).

Example 2: Differences in Complexation of Mn in Contrast Agents

It was found that a 2:1 complex of 1-OH bisphosphonate and $Mn^{2+}$ is thermodynamically favored. By varying stoichiometry during synthesis, no additional complexation of $Mn^{2+}$ is observed when the ratio of bisphosphonate to $Mn^{2+}$ is raised above 2:1. (FIG. 3A)

Free $Mn^{2+}$ is determined by measuring solvent $T_2$ as a function of time, since $r_2$ of $Mn^{2-}$ is 30-fold that of fully chelated, monohydrated $Mn^{2+}$ (Caravan et al., Mol. Imaging 2009, 4:89). Relaxivity measurements of 1-OH bisphosphonate:Mn2+ complexes and $MnCl_2$ were performed at 7 T at 22° C. in 2 mM Tris buffered $ddH_2O$. Sodium-containing solutions were titrated with NaOH to pH 7.0. Sodium-free solutions were titrated to neutral pH with the corresponding cation base (choline or meglumine). Stock solutions for each sample were prepared with 20 mM Mn2+. $r_1$ and $r_2$ were calculated from conventional MR fast spin echo-based mapping methods for sample concentrations at 200 micromolar.

It was found that alkali metal cations increase the stability of the 2:1 bisphosphonate:$Mn^{2+}$ complex. Heteronuclear complexes containing at least one $Na^+$ cation and at least one $Ca^{2+}$ cation form the most stable 2:1 complexes, resulting in complete chelation of mono-hydrated $Mn^{2+}$ without excess ligand.

Example 3: Metal-complexed 1-hydroxy ethane-1,1-diphosphonic Acid-Derived Small Molecule Drugs for Modified Biodistribution, Diagnostic Imaging and Enhanced Therapeutic Activity Mn bisphosphonate complexes afford new opportunities for creating an array of novel molecular imaging probes for MR imaging and image-guided therapy. 1-hydroxylethyl-enediphosphonates are readily amenable to coupling, either through their R2 group off the central carbon or vis. phosphate esterification, and can therefore be derivatized with many existing small molecule drugs that possess known targeting and/or therapeutic activities.

In addition to treatment of bone-related conditions, bisphosphonates have more recently shown significant promise as chemotherapeutic adjuncts for several malignancies. The mechanism of action is believed to be through inhibition of farnesyl disphosphate synthase (FDPS) and/or other intracellular enzymes that normally utilize pyrophosphate, the structural analogue of bisphosphonate. With the intracellular co-transport of bisphosphonates complexed with tumor-avid small molecules and Mn, bisphosphonates enable both molecular imaging and a second therapeutic activity in addition to that of the parent molecule.

Finally, it is worth noting that free Mn is believed to be toxic neurologically if allowed to accumulate to high concentrations in certain neuronal populations. When concentrations of Mn exceed the intracellular binding pool, Mn, as with Fe and other transition metals, fuels Fenton-mediated free radical production, particularly in the co-presence of elevated redox-active species such as $H_2O_2$, ascorbate, and quinones. Since Mn accumulation in tissues is readily visualized with MRI, however, selective delivery of Mn-containing agents is easily monitored. (Indeed, in whole animal MRI experiments with high-resolution quantitative $T_1$ mapping, no CNS accumulation of Mn was ever observed after administration of Mn bisphosphonate even at >10× dose.) In the disclosed inventions, selective accumulation of Mn in cancer cells, confirmed by MRI, thus enables yet another therapeutic opportunity through controlled redox-mediated cytotoxicity, activated by adjuvant administration of tumor-selective redox drivers such as high dose parenteral ascorbate and/or quinone reductase II inhibitors.

Figure 5:
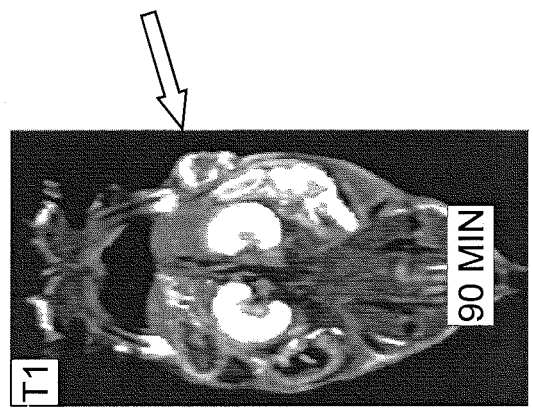
FIG. 5. Dynamic contrast enhancement of 4T1 tumor after i.v. admin of 1-hydroxybisphosphonate:Mn complex linked to HSP90 inhibitor as in Scheme 1C, 25 mg/kg. Graph on left depicts relative change in T1 enhancement in tumors after labeled drug (n=5) and after Mn:ETID complex alone (n=6).
Figure 5:
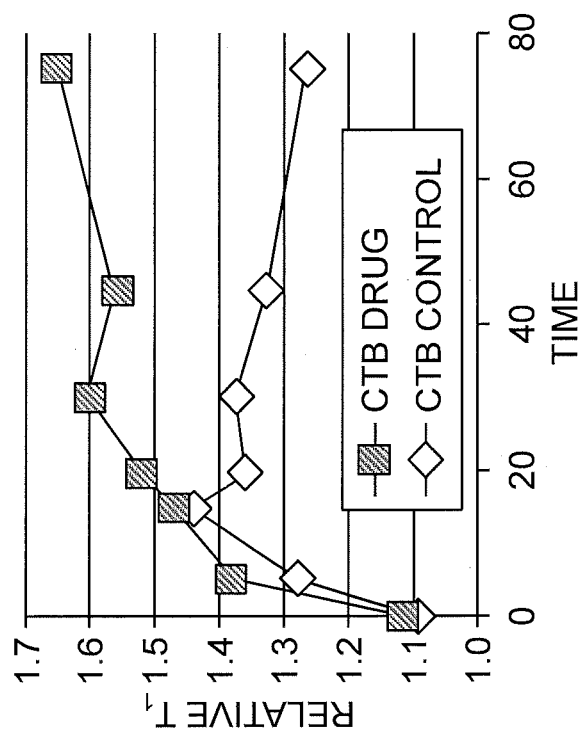

Several synthetic strategies were used for labeling small molecule drugs either directly or via polyethyleneglycol (PEG) linkers. Two lead complexes, the first with a medronate analogue (Scheme 1B) via the amine-terminated PEG linker, and the second an etidronate analogue coupled through the COOH-terminated PEG linker (Scheme 1C), have now been synthesized, characterized and studied preliminarily in vivo. Pilot data for both complexes show progressive accumulation of enhancement in 4T1 tumors that is greater than what is seen for the paramagnetic coordination complex alone (FIG. 5). Preliminary data on administration of the untethered HSP90i compound 30 min in advance of paramagnetic administration also suggest some competitive inhibition of PM complex from the parent drug.

Scheme 1. Bisphosphonate functionalized HSP90 inhibitors. A, Cancer cell-selective, 'high accumulating' HSP90 inhibitor is derivatized with a short PEG-linker, and linked to an amine group that does not interfere with the molecule's HSP90 selectivity. B, medronate analogue is then linked to the PEG. C, 1-hydroxybisphosphonate analogue is linked to the PEG.

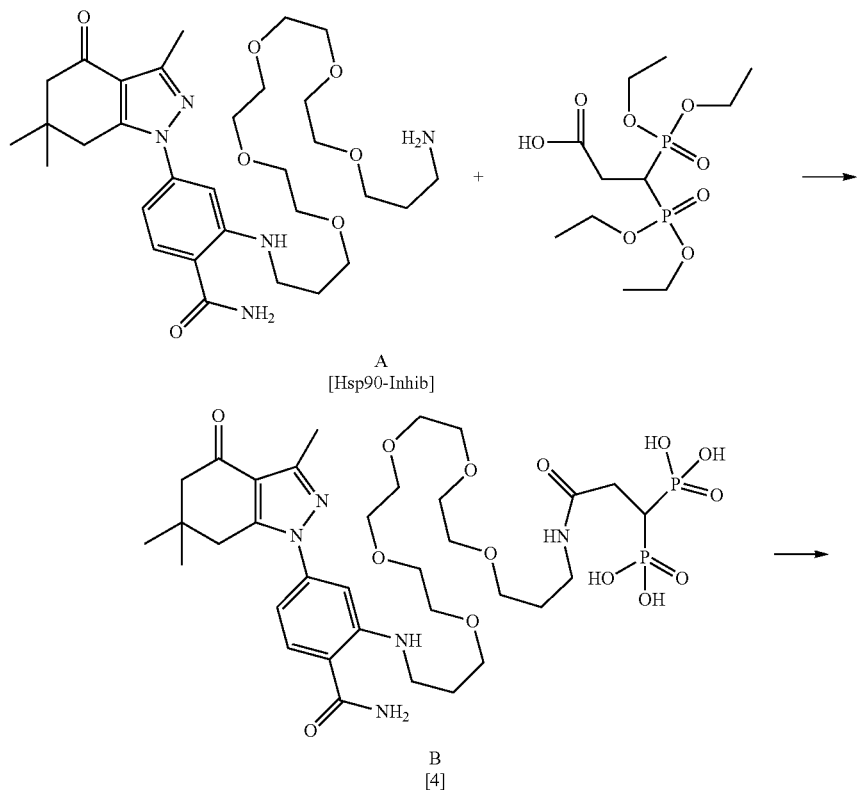

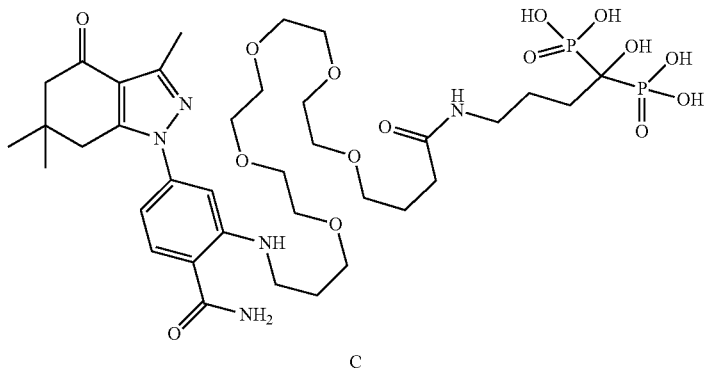

C

Also synthesized was a 1-hydroxybisphosphonate derivative of the 4-aminoquinoline quinone reductase 2 inhibitor Chloroquine, another well-characterized small molecule drug with high accumulative selectivity in many cancers. In addition to selective accumulation, Chloroquine has shown recent promise as an effective adjunctive in chemotherapy trials.

Scheme 2. 1-hydroxybisphosphonate derivative of the 4-aminoquinoline chloroquine.

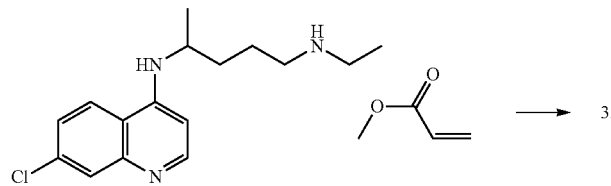

1-hydroxybisphosphonate functionalization of small molecule drugs may be accomplished through either direct conjugation of these molecules or through molecular bridges (e.g., PEG) linked to both these small molecules and 1-hydroxybisphosphonate analogues. They may be used to form subsequent metal complexation useful for diagnostic and/or therapeutic applications. Scheme 3 and Scheme 4 present example methods for direct linkages to an HSP90 inhibitor and to an FDA-approved drug lapatinib, a 'high-accumulating' tyrosine kinase inhibitor used for the treatment of some breast cancers.

Scheme 3. Commercially available 1-hydroxybisphosphonates with amine terminal R2 groups (above) and proposed synthesis for direct coupling of bisphosphonate to HSP90 inhibitor.

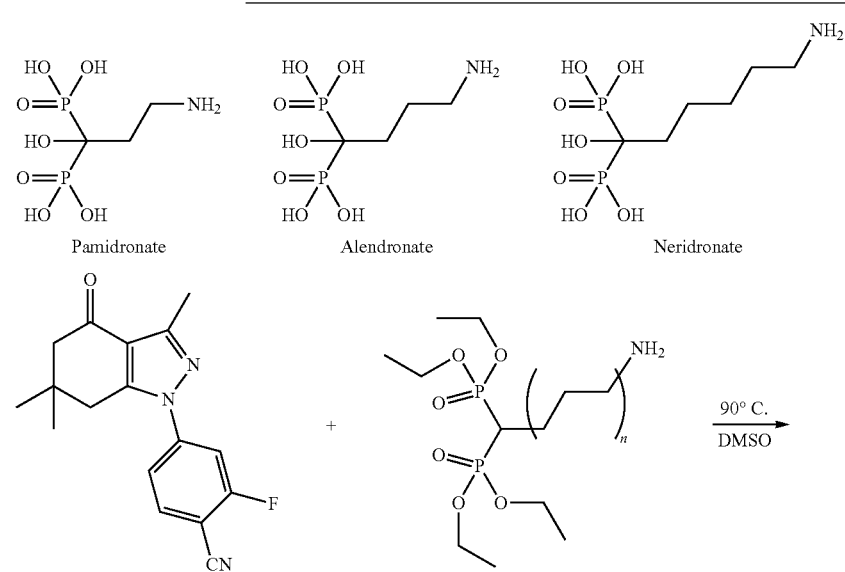

-continued
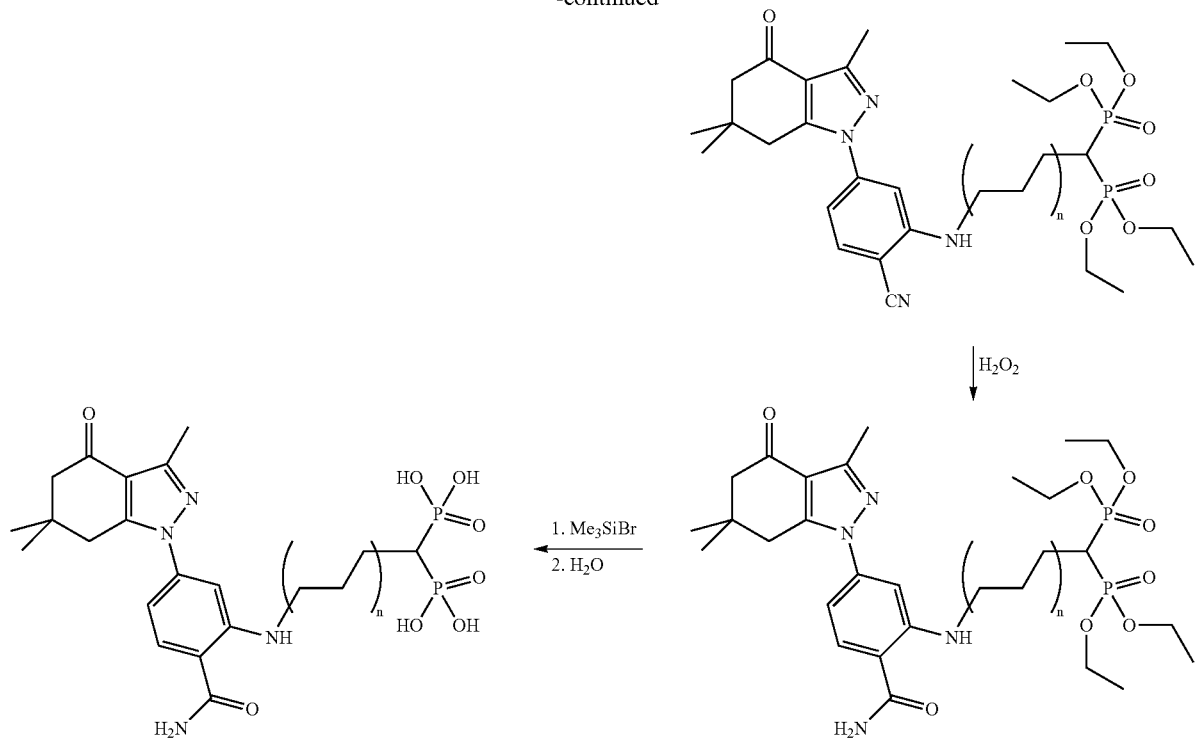
Scheme 4. Proposed synthesis for direct 1-hydroxybisphosphonate coupling of lapatinib.
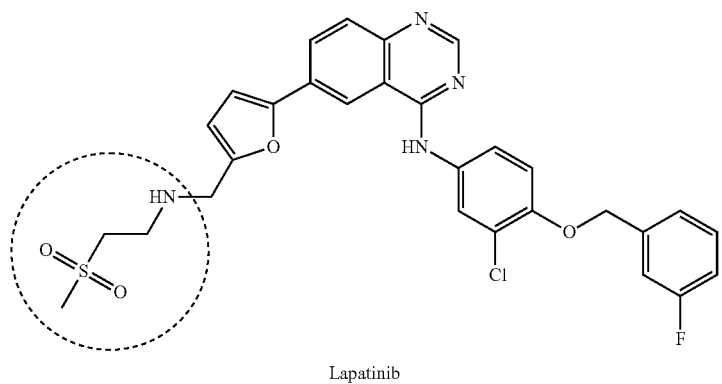
Lapatinib
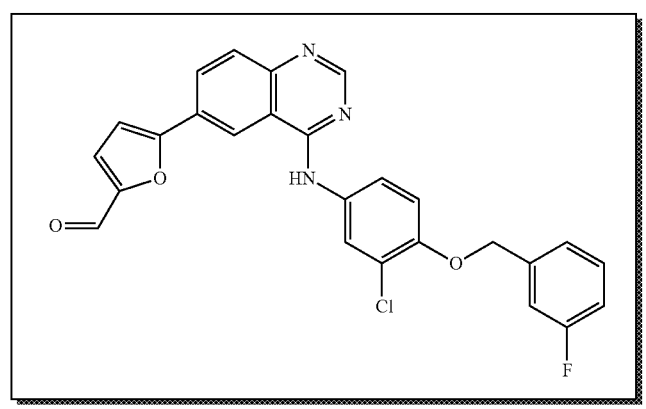

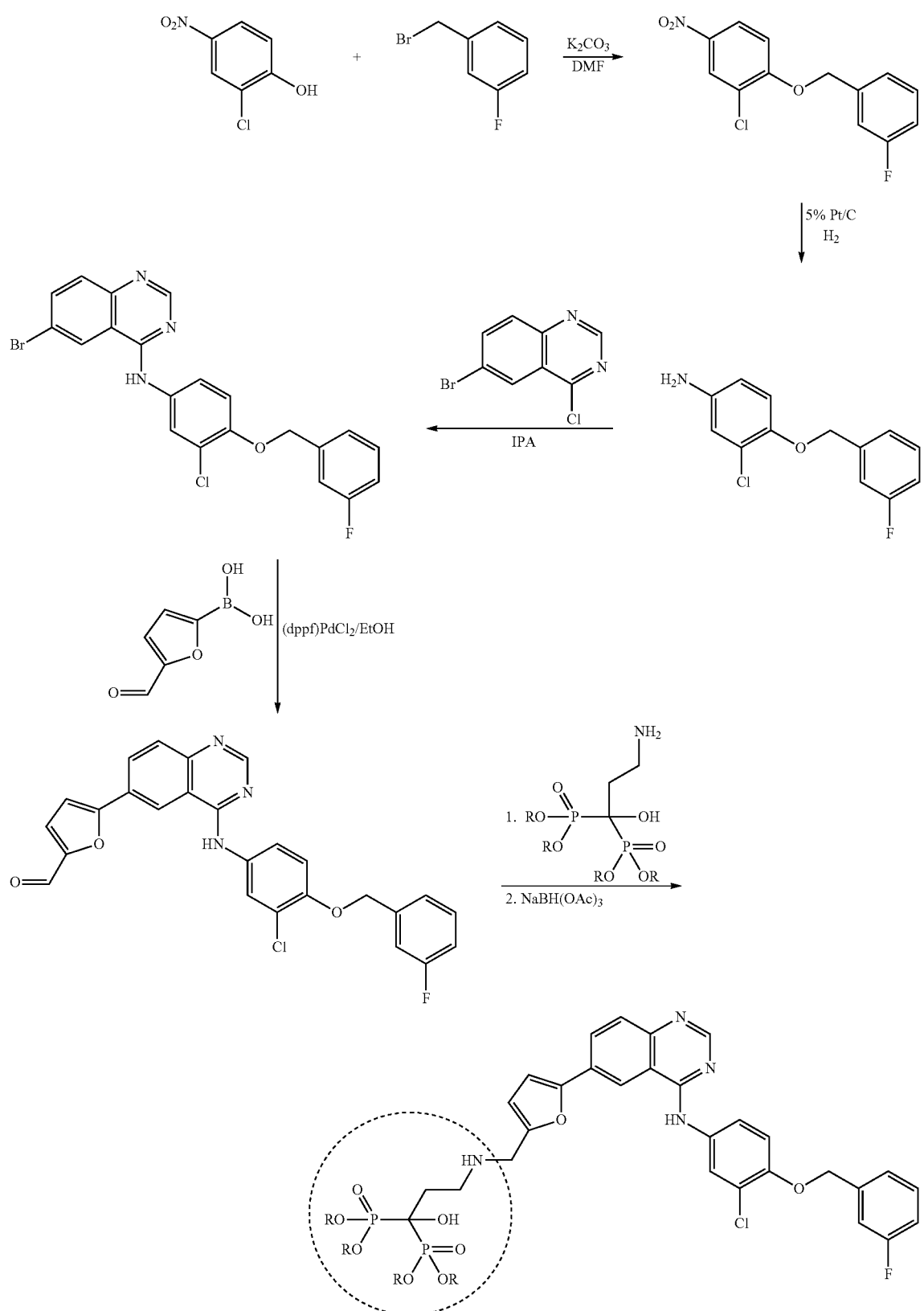
-continued
R = H or C₂H₅

Figure 7B:
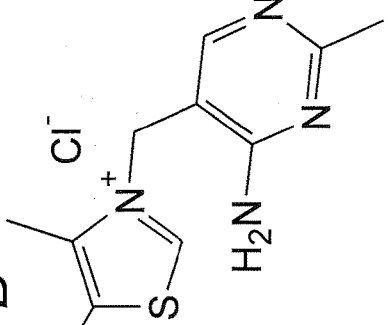
FIGS. 7A-7D. Paramagnetic $Fe(P_2O_7)_2$ complex and thiamine iron pyrophosphate derivative.
Figure 7B:
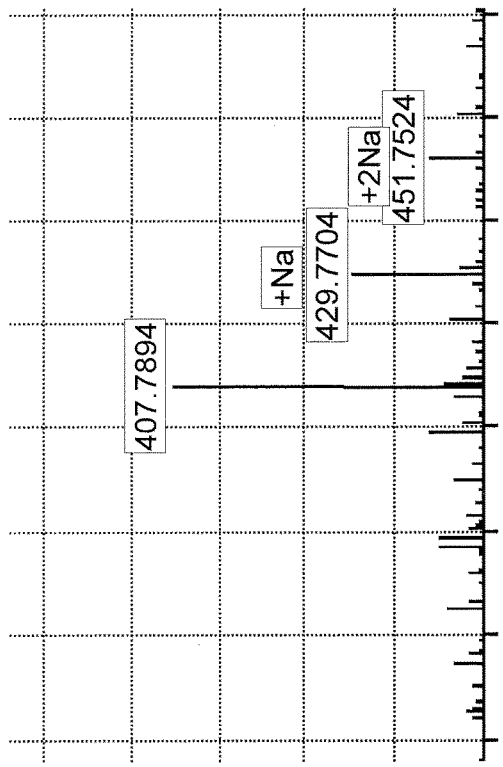
Figure 7A:
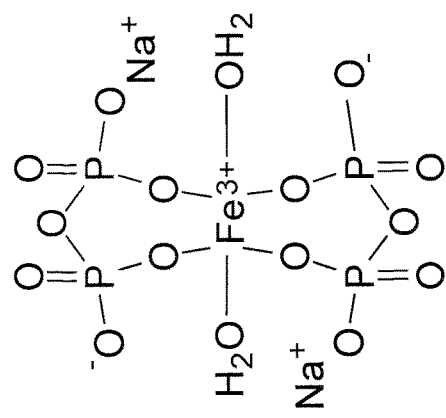
Figure 7C:
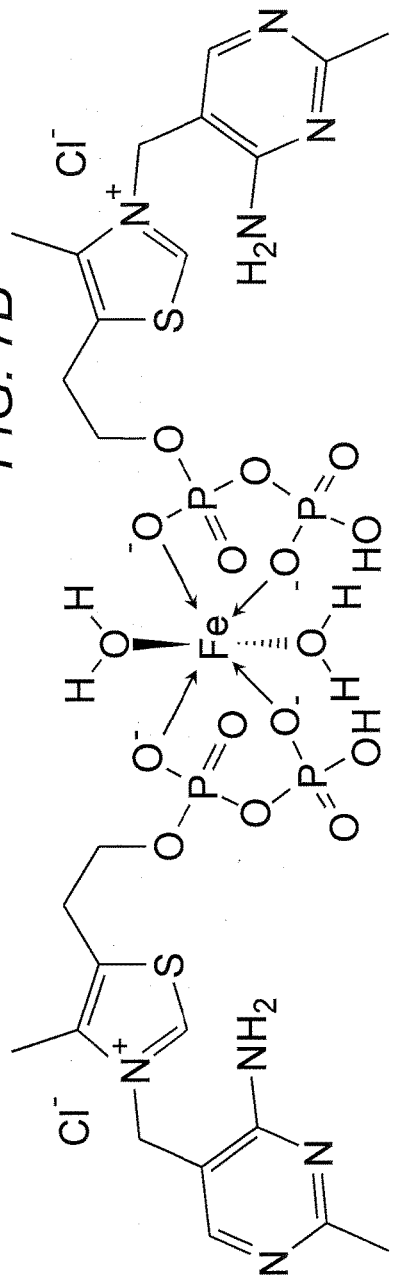
Figure 7D:
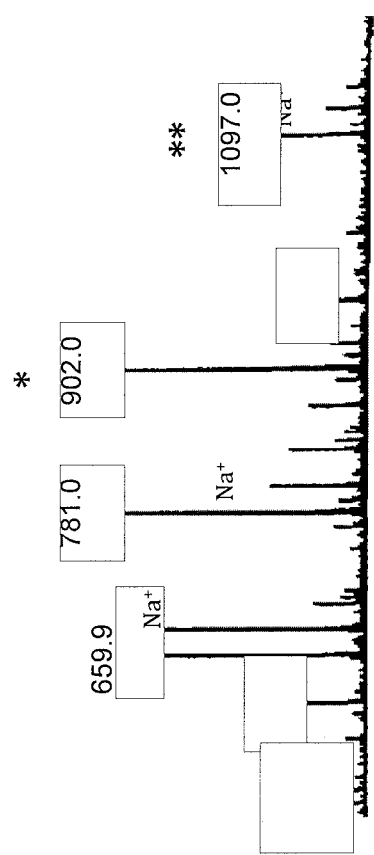

Example 4: High Spin Iron Pyrophosphate Complex and its Derivatives for Diagnostic and Therapeutic Application The interaction between Fe(III) and pyrophosphate ($P_2O_7$) was explored. $P_2O_7$, a ubiquitous diphosphate tetraanion, is one of the strongest known chelators of Fe(III). A protocol was developed for synthesis of a paramagnetic scaffold incorporating two $P_2O_7$ anions with one Fe(III), yielding a high-spin, octadehedral Fe(III) complex coordinating two inner sphere waters (q=2) (FIG. 7A). At 7T field strength, $r_1$ for this low molecular weight complex is 5.2 $mM^{-1}s^{-1}$, which is equivalent to the relaxivity of the strongest commercial Gd(III) agent gadobutrol at identical field strength. At a more clinically relevant field strength of 1.5 T, $r_1$ for the $Fe(P_2O_7)_2$ complex increases to 35 $mM^{-1}s^{-1}$, a relaxivity not previously reported for any Fe(III)-based contrast agent. The impressive contrast enhancement of this scaffold is likely related to its unusually stable coordination of the two inner waters, as well as significant outer sphere contributions mediated through extensive hydration of phosphate groups. The stability constant (log K1) for the $Fe(P_2O_7)_2$ complex is estimated to be >22 at neutral pH and room temperature based on competition experiments with EDTA (log K1=26). Coordination strength is therefore higher than commercial macrocyclic Gd(III) complexes, which typically have log K1s~17. The stability of $Fe(P_2O_7)_2$ is consistent with previously reported complexes for pyrophosphate and Fe(III) at various stoichiometries.

Animal experiments reveal rapid renal clearance of the $Fe(P_2O_7)_2$ complex, providing further evidence the complex remains intact in vivo. Free Fe(III) released into the blood pool will no longer clear efficiently through the kidneys, nor remain capable of producing T1 enhancement. With rapid intravenous bolus administration at >10 times an estimated therapeutic dose of 25 mg/kg, respiratory rate, heart rate/rhythm and behavior are unchanged acutely, at 24 hours, and after 1 week.

Pyrophosphate, when linked to various ligands, retains the capacity to form the paramagnetic $Fe(P_2O_7)_2$ scaffold. Thus thiamine, inosine, and guanine pyrophosphate derivatives are all capable of forming analogous $Fe(P_2O_7)_2$ paramagnetic complexes. Thiamine pyrophosphate (ThPP), in a 2:1 complex with Fe(III) forms a paramagnetic moiety also equally stable in vivo. Besides illustrating the versatility of this paramagnetic scaffold, these experiments also suggest thiamine as a potential targeting moiety for cancer cells.

Example Synthesis of High Spin Fe (III) Pyrophosphate Complex

To a desired final volume of double distilled water and under constant stirring add one equivalent of ferric salt (e.g., ferric chloride, ferric acetate, ferric citrate, etc.) to two equivalents of sodium pyrophosphate dibasic. The solution should remain cloudy. Raise the temperature of the solution to 80 or 90° C. under vigorous stirring, then add three equivalents of sodium bicarbonate. This should be done in measured fashion because of resultant $CO_2$ production. With continued vigorous stirring under heat, the solution will eventually clear over ~2-20 minutes, retaining a faint green-yellow hue. The time to clear and the degree of hue are dependent on the starting concentrations of reagents and the relative amount of heat applied. As the solution clears, stirring should continue as the sample is removed from heat. The final pH should be ~7.0-7.2 when the solution reaches room temperature.

Additional transient elevation of the pH to 8.0 with sodium hydroxide or other base can be performed on a sample of the final solution to test for any free iron, which will precipitate as iron oxide. With high quality reagents, the above steps should result in complete complexation of iron and no precipitation.

If desired, solid product may be easily precipitated and isolated with polar organic solvents such as acetone, methanol, or ethanol at a ratio 4:1. The sample may then be dried gently under heat or freeze-dried under vacuum. The solid material will remain shelf-stable indefinitely but is notably hygroscopic.

Example Synthesis of Paramagnetic Thiamine Pyrophosphate 40 mM thiamine pyrophosphate and 40 mM meglumine are dissolved in $_{dd}H2O$ at room temp under constant stirring. 20 mM $FeCl_3$ in $H_2O$ is added slowly under constant stirring. 60 mM $NaHCO_3^-$ is then added. Final pH is between 6.5-7. Sample is cooled, freeze dried/lyophilized until yielding gold-orange-brown, dispersed glassy microbeads. As dried, the complex remains stable for more than several months at room temperature.

The foregoing is illustrative of the present invention, and is not to be construed as limiting thereof. The invention is defined by the following claims, with equivalents of the claims to be included therein.

That which is claimed is:

1. A magnetic resonance imaging (MRI) contrast agent comprising a compound having a structure represented by:

wherein,

X is Mn(II) and Y and Z are each independently a bisphosphonate of the formula:

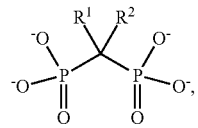

wherein: $R^1$ is —OH, and $R^2$ is selected from the group consisting of: H, alkyl, aminoalkyl, alkylaminoalkyl, arylalkyl, and heteroarylalkyl wherein said compound has a stoichiometry of 1:2 (Mn(II):bisphosphonate);

wherein said compound is a salt comprising at least one alkali metal and at least one alkaline earth metal, and wherein the contrast agent has a molecular weight of less than 2,000 daltons.

2. The MRI contrast agent of claim 1, wherein the contrast agent has a molecular weight of less than 800 daltons.

3. The MRI contrast agent of claim 1, wherein the compound is octahedral.

4. The MRI contrast agent of claim 1, wherein the compound is a monohydrate or a dihydrate.

5. The MRI contrast agent of claim 1, wherein the alkali metal comprises Na+ or K+.

6. The MRI contrast agent of claim 1, wherein said bisphosphonate is etidronate.

7. The MRI contrast agent of claim 1, comprising:
at least one water coordinated with said Mn(II).

8. The MRI contrast agent of claim 1, wherein said MRI contrast agent has an $r_2$ relaxivity of 5 to 18 $mM^{-1}sec^{-1}$ measured at 7 Tesla, 22 degrees Celsius, in 2 mM Tris buffered $ddH_2O$, pH 7.0.

9. The MRI contrast agent of claim 1, wherein said alkaline earth metal is selected from calcium and magnesium.

10. The MRI contrast agent of claim 9, wherein said alkali metal comprises sodium.

11. The MRI contrast agent of claim 1, wherein said compound is coupled to one or more therapeutic agents.

12. The MRI contrast agent of claim 11, wherein said one or more therapeutic agents are covalently coupled to Y and/or Z.

13. A composition comprising the MRI contrast agent of claim 1 in a pharmaceutically acceptable carrier.

14. The composition of claim 13, wherein said composition is formulated for intravenous or intraarterial administration.

15. The composition of claim 13, wherein said pharmaceutically acceptable carrier is water or phosphate buffered saline.

16. The composition of claim 13, wherein said composition has a pH of from 6.0 to 8.0.

17. The composition of claim 13, wherein said composition has a pH of from 7.0 to 7.4.

18. A method of performing a magnetic resonance imaging (MRI) scan on a subject comprising administering the composition of claim 13 to said subject prior to and/or during said MRI scan.

19. A method of administering a therapeutic agent to a subject in need thereof, comprising administering the MRI contrast agent of claim 1 to said subject in a treatment effective amount.

20. The method of claim 19, further comprising detecting the MRI contrast agent with MRI in said subject.

* * * * *

UNITED STATES PATENT AND TRADEMARK OFFICE
CERTIFICATE OF CORRECTION

| | |
|---|---|
| PATENT NO. | : 10,293,062 B2 |
| APPLICATION NO. | : 15/463688 |
| DATED | : May 21, 2019 |
| INVENTOR(S) | : Christopher David Lascola |

It is certified that error appears in the above-identified patent and that said Letters Patent is hereby corrected as shown below:

In the Claims

Column 19, Line 29, Claim 19: Please correct "claim 1" to read -- claim 11 --

Signed and Sealed this
Twenty-ninth Day of October, 2019

Andrei Iancu
*Director of the United States Patent and Trademark Office*